US009057721B1

(12) United States Patent
Marion, Jr.

(10) Patent No.: US 9,057,721 B1
(45) Date of Patent: Jun. 16, 2015

(54) FAIL-SAFE ASSAY DEVICE FOR CONTROLLED AND ORDERED DELIVERY OF REAGENTS TO A SAMPLE

(71) Applicant: Point of Care Technologies, LLC, Greenville, SC (US)

(72) Inventor: William Francis Marion, Jr., Greenville, SC (US)

(73) Assignee: Point of Care Technologies, LLC, Greenville, SC (US)

( * ) Notice: Subject to any disclaimer, the term of this patent is extended or adjusted under 35 U.S.C. 154(b) by 0 days.

(21) Appl. No.: 14/271,020

(22) Filed: May 6, 2014

Related U.S. Application Data

(60) Provisional application No. 61/820,285, filed on May 7, 2013.

(51) Int. Cl.

| | |
|---|---|
| ***G01N 15/06*** | (2006.01) |
| ***G01N 33/00*** | (2006.01) |
| ***G01N 33/48*** | (2006.01) |
| ***G01N 33/50*** | (2006.01) |

(52) U.S. Cl.
CPC .................................... *G01N 33/50* (2013.01)

(58) Field of Classification Search
USPC .......... 422/50, 68.1, 547, 549, 550, 554, 502, 422/503, 504, 559; 436/43
See application file for complete search history.

(56) References Cited

U.S. PATENT DOCUMENTS 4,813,432 A 3/1989 Saint-Amand
5,827,675 A 10/1998 Skiffington et al.
6,043,047 A 3/2000 Foote et al.
6,248,294 B1 6/2001 Nason
6,551,834 B2 4/2003 Carpenter et al.
6,656,428 B1 12/2003 Clark et al.
2003/0143752 A1 7/2003 Feldsine et al.
2005/0084842 A1 4/2005 O'Connor
2005/0131314 A1 6/2005 Hird et al.
2005/0136553 A1 6/2005 Kaylor et al.
2006/0160170 A1 7/2006 Giordano
2007/0031914 A1 2/2007 Zhu et al.
2008/0076169 A1 3/2008 Miles et al.
2008/0260581 A1 10/2008 Rosman et al.
2008/0302193 A1 12/2008 Bommarito et al.
2009/0232702 A1 9/2009 Wu et al.
2010/0274155 A1 10/2010 Battrell et al.
2011/0143365 A1 6/2011 Buchanan
2012/0269701 A1 10/2012 Linder et al.
2012/0329081 A1 12/2012 Bennion et al.

FOREIGN PATENT DOCUMENTS

WO 2012025729 3/2012

*Primary Examiner* — Brian J Sines
(74) *Attorney, Agent, or Firm* — Richard A. Brisbin; Haynsworth Sinkler Boyd, P.A.

(57) ABSTRACT

An assay device may include a first cylinder that includes a first end that is closed and a second, opposite end that is open. The first cylinder may include one or more reservoirs that are compressible and store one or more reagents. The device may include a test chamber to which the reservoirs are connected, and in which the sample can be inserted to perform the assay; and a second cylinder that includes a third end that is closed and a fourth, opposite end that is open. The fourth end may fit within the second end to enable the second cylinder to be attached to, and rotate within, the first cylinder. The third end may include a member that compresses the reservoirs, in a predetermined order, as the second cylinder is rotated within the first cylinder to cause the reagents to flow, to the test chamber, in the predetermined order.

10 Claims, 5 Drawing Sheets

FAIL-SAFE ASSAY DEVICE FOR CONTROLLED AND ORDERED DELIVERY OF REAGENTS TO A SAMPLE

BACKGROUND

Portable, hand held, and/or disposable devices used to perform real time or near-real time medical, chemical, or biological assays (e.g., at the point of care, in the field, at a crime scene, in a laboratory, etc.) may enable a practitioner (e.g., a technician, an investigator, a paramedic, a soldier, a nurse, a doctor, a veterinarian, etc.), to apply one or more reagents to a sample taken from a subject (e.g., a sample obtained from the subject's throat, urine, feces, vagina, ear, wound, blood, etc.), from a surface of an object, from a water supply, etc. The practitioner may insert the sample into the device and may perform an assay operation on the sample by causing the device to deliver the one or more reagents to the sample, for example, to test for the presence of certain biological matter, chemicals, contaminants, etc.

Devices can be used to perform a particular assay operation by delivering multiple reagents, stored within the device, to the sample. The device may permit the reagents to be delivered to the sample in an order or manner that is different than a particular order or manner associated with the particular assay operation, which may cause the particular assay operation to be performed incorrectly.

SUMMARY

According to one possible implementation an assay device may perform an assay on a sample, the assay device may include a first cylinder that includes a first end that is closed and a second, opposite end that is open. The first cylinder may include a first reservoir that stores a first reagent, a second reservoir that stores a second reagent, and a transparent test chamber to which the first reservoir and the second reservoir are connected, and in which the sample can be inserted to perform the assay. The assay device may also include a second cylinder that includes a third end that is closed and a fourth, opposite end that is open. The fourth end may fit within the second end and enable the second cylinder to be attached to, and rotate within, the first cylinder. The second cylinder may include a first lock associated with the first reservoir and a second lock associated with the second reservoir. The first lock and the second lock may enable at least one of: the first reagent and the second reagent, respectively, to be precluded from flowing into the test chamber when the second cylinder is in a first rotational position relative to the first cylinder; the first reagent to flow to the test chamber and precluding the second reagent from flowing to the test chamber when the second cylinder is turned to a second rotational position relative to the first cylinder; or the second reagent to flow to the test chamber when the second cylinder is turned to a third rotational position relative to the first cylinder.

According to another possible implementation, an assay device may perform an assay on a sample. The assay device may include a first cylinder that includes a first end that is closed and a second, opposite end that is open. The first cylinder may also include one or more reservoirs and a test chamber. The one or more reservoirs may be compressible and store one or more reagents, and the test chamber may be connected to the one or more reservoirs, and receive the sample on which the assay is to be performed. The assay device may also include a second cylinder includes a third end that is closed and a fourth, opposite end that is open. The fourth end may fit within the second end and enable the second cylinder to be attached to, and to rotate within, the first cylinder. The third end may include at least one member that compresses the one or more reservoirs, in a predetermined order, as the second cylinder is rotated within the first cylinder. Compressing the one or more reservoirs may cause the one or more reagents to flow to the test chamber according to the predetermined order.

DETAILED DESCRIPTION

Figure 1:
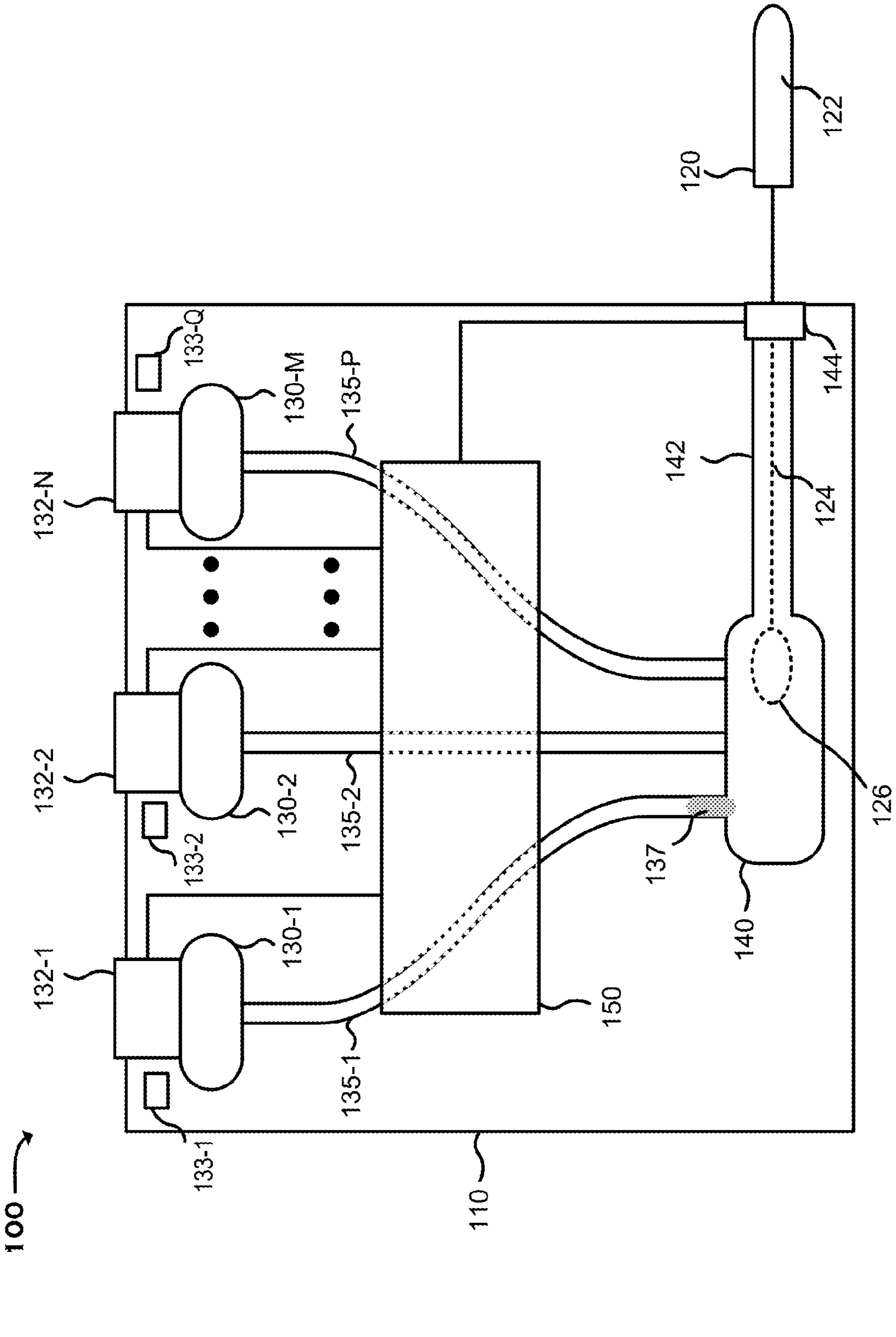
FIG. 1 is a diagram of an example functional assay device in which the systems and/or methods, described herein, may be implemented.

The systems, methods, technologies, and/or techniques (hereinafter referred to as the "systems and/or methods"), described herein, may enable an assay operation to be performed on a sample using two or more reagents while ensuring that such reagents are applied in a particular predetermined order, amount, and/or flow rate based on a type of assay operation being performed. The systems and/or methods may include an assay device that includes a sample component that can be used by a practitioner, of the assay device, to obtain a sample from a subject at the point of care (e.g., a sample taken from the subject's throat, urine, feces, vagina, ear, wound, etc.) and/or from inanimate objects within the field (e.g., to check for contaminates, blood, drugs, or other materials or evidence on a surface, in the water supply, etc.). The point of care and/or the field may include, without limitation, a hospital, doctor's office, clinic, battlefield, a transport (e.g., ship, plane, train, bus, etc.) crime scene, outdoor or athletic events, etc.

Additionally, or alternatively, the systems and/or methods may enable the delivery of two or more reagents, stored within the assay device, to a test chamber in which the sample has been inserted to treat and/or saturate the sample for the purposes of performing an assay operation corresponding to a medical, biological, and/or chemical analysis of the sample. Delivery of such reagents to the test chamber and/or sample may be by forced delivery and regardless of any forces due to gravity or other accelerations, orientation or movement of the assay device, etc. The systems and/or methods may enable the delivery of the reagents to occur in a particular order, and/or in a controlled and/or tunable manner (e.g., by controlling or tuning flow parameters of the reagents, associated with instantaneous, average or changes in flow rate, pressure, flow velocity and/or acceleration, a spray pattern into the test chamber and/or on the sample). Such control and/or tunability may include controlling flow parameters of reagents of varying viscosities and/or temperatures to affect the manner in which the reagent is delivered and/or injected on to the surface of or into the sample.

The systems and/or methods may include a fail-safe mechanism to ensure that two or more reagents are injected in a predetermined order. In the event that a practitioner, associated with the assay device, attempts to deliver the reagents in an order that is different than the predetermined order, the systems and/or methods may prevent the reagents from being delivered in the different order. Additionally, or alternatively, the assay device may have a capacity to handle a range of sample sizes including conventionally-sized swabs and/or other types sample collecting devices or swabs that are larger than, the same size as, or smaller than the conventional sized swab. The systems and/or methods may also, or alternatively, enable the assay device to be made in various sizes and/or shapes to accommodate or house large quantities of reservoirs to store large quantities of different types of reagents (e.g., 3 types, 5 types, 10 types, 20 types, etc. of reagents). The systems and/or methods may enable the assay device to operate in a range of environment and/or climates, and/or to preserve the sterility the reagents, components through which such reagents flow, the test chamber, and/or sample component.

FIG. 1 is a diagram of an example assay device 100 (hereinafter "device 100") in which the systems and/or methods, described herein, may be implemented. As shown in FIG. 1, device 100 may include functional components such as, for example, a housing component 110 (hereinafter referred to as "housing 110") a sample component 120, a group of reagent reservoir components 130-1, . . . , 130-M (collectively referred to herein as "reservoirs 130," and individually as "reservoir 130") (where M≥1) a group reagent button components 132-1, . . . , 132-N (collectively referred to herein as "buttons 132" and individually as "button 132") (where N≥1), a group reagent delivery indicator components 133-1, . . . , 133-Q (collectively referred to herein as "indicators 133" and individually as "indicator 133") (where Q≥1) a group of reagent channel components 135-1, . . . , 135-P (collectively referred to herein as "channels 135," and individually as "channel 135") (where P≥1), a flow control nozzle component 137 (hereinafter referred to collectively as "nozzles 137" and individually as "nozzle 137"), an assay test chamber 140 (hereinafter referred to as "chamber 140") and a reagent control mechanism 150 (hereinafter referred to as a "control mechanism 150").

The number of functional components, illustrated in FIG. 1, is provided for explanatory purposes only. In practice, there may be additional functional components, fewer functional components, different functional components, or differently arranged functional components than illustrated in FIG. 1. Also, in some implementations, one or more of the functional components of device 100 may perform one or more functions described as being performed by another one or more of the functional components of device 100. For example, chamber 130, button 132, and/or a respective control mechanism 150 may be integrated into a single component. Additionally, or alternatively, one or more reservoirs 130, buttons 132, and/or control mechanisms 150 may be integrated into sample component 120 in addition to or instead of housing 110.

Housing 110 may include any material, frame, or structure such as metal, plastic, composite, or the like that is of sufficient strength and rigidity to enable the components described herein to be attached and/or used by a practitioner of device 100. Housing 100 may assume any shape or volume such as, for example, a cube, sphere, disk, cylinder, etc.

Sample component 120 may include a handle 122, a member 124 and a swab 126. Sample component 120 may be used to obtain a sample from a subject. For example, a practitioner of device 100 may use sample component 120 to obtain a throat culture from a subject by holding handle 122 and inserting member 124 and swab 126 into the subject's mouth or other applicable locations on a subject form which a sample can be obtained (e.g., from the subject's throat, mouth, tongue, rectum, urine, nose, vagina, ears, wound, blood, etc.). Sample component 120 may also, or alternatively, be used to obtain samples from an inanimate object (e.g., a surface of a table, a water source, objects within a crime scene, etc.).

Reservoir 130 may include a cavity that is made of any material, such as plastic, foil, rubber, etc. that is capable of being shaped (e.g., a bulb, a hollow sphere, etc.) in a manner that enables storage or portability of a liquid reagent. Reservoir 130 may, in one example, be made of a pliable material such that when reservoir 130 is compressed, the reagent is evacuated via channel 135 through which the reagent flows to chamber 140. Button 132 may include any mechanism that can be used to compress reservoir 130, such as, for example, a syringe, a plunger, a frangible bulb, etc. Indicator 133 may include any mechanism that indicates whether a button 132 or chamber 130 has been compressed and/or a reagent, stored in chamber 130, has been delivered to chamber 140. For example, indicator 133 may change in appearance (e.g., change in color, cause a light bulb and/or a light emitting diode (LED) to emit light and/or change color, etc.) when button 132 or chamber 130 has been compressed and/or a reagent has been delivered to chamber 140. In one example, reservoir 130 may be a flexible and/or frangible bulb and/or reservoir that can be compressed directly by a practitioner without button 132. Button 132 may also, or alternatively, be connected (e.g., mechanically, electrically, etc.) with control mechanism 150 for the purposes of communicating to mechanism 150 an indication that button 132 and/or reservoir 130 is being or has been compressed. Reservoir 130 and/or button 132, when depressed, may enable reagent to flow to chamber 140 and via channel 135 regardless of the orientation of device 100 and/or the direction of a pull caused by a gravitational field or some other acceleration.

Nozzle 137 may include any component through which a reagent flows to reservoir 140 from channel 135. Nozzle 137 may include a particular diameter or cross sectional area or pattern (e.g., a straight-through shape, a venturi, etc.) through which the reagent flows which enables nozzle 137 to control a manner in which the reagent flows into chamber 140, such as, for example, a rate of mass flow, a flow pressure, a spray pattern, a velocity, an acceleration, etc. in connection with the reagent flowing into chamber 140. Nozzle 137 may also, or alternatively, act as a valve that permits reagent to flow from channel 135 to chamber 140, but may not permit any reagent to flow from chamber 140 to channel 135.

Chamber 140 may include a cavity that is capable of holding a swab 126 and/or member 124, as well as receive one or more reagents from one or more channels 135. Chamber 140 may include an entry tube 142 through which swab 126 and/or member 124 can be inserted. Chamber 140 may also, or alternatively, include an interface 144 that is connected to entry tube 142 and to which sample component 120 connects when inserted into housing 110. Interface 144 may, for example, be mechanically, electrically, or optically connected to control mechanism 150 for the purposes of communicating an indication when sample component 120 is being connected to or disconnected from housing 110, and/or when swab 126 has been inserted into or removed from chamber 140. Interface 144 may also, or alternatively, include a component that prevents reagent, within chamber 140, from flowing out of chamber 140 and/or entry tube 142. Interface 144 may also, or alternatively, include a component that maintains a sterile environment within chamber 140 and/or entry tube 142 before swab 126 on which a sample has been collected, is inserted into chamber 140.

All or a portion of chamber 140 may be made of a material that is transparent to permit a practitioner of device 100 to observe swab 126, a sample collected on swab 126, and/or the reagents that have flowed into chamber 140. Such materials may include dielectric constants that cause the material to be transparent or semi-transparent within the visible light spectrum (for viewing by an unaided eye), at other optical frequencies such as infrared or ultraviolet (e.g., for viewing with the aide of an infrared or ultraviolet detector, photo diode, etc.), or radiation bands (e.g., millimeter waves, microwaves, X-rays, gamma rays, etc.).

Control mechanism 150 may include one or more, potentially distributed mechanical, electrical, and/or optical components that control the manner in which two or more reagents, stored within reservoirs 130, are permitted to flow into chamber 140 via channel 135 and/or nozzle 137. For example, control mechanism 150 may include a component that ensures that two or more reagents flow in a particular order into chamber 140. In one example, control mechanism 150 may permit a first reagent, stored in a first reservoir 130, to flow to chamber 140 before permitting a second reagent, stored in a second reservoir 130 to flow to chamber 140. In the event that a practitioner of device 100 attempts to cause the second reagent to flow prior to the first reagent, control mechanism 150 may not permit such second reagent to flow to the chamber 140 prior to the first reagent. Additionally, or alternatively, control mechanism 150 may permit two or more reagents to simultaneously or concurrently flow to chamber 140 and may prevent a particular, different reagent from flowing simultaneously or concurrently with the two or more reagents to chamber 140. Additionally, or alternatively, control mechanism 150 may prevent any reagent from flowing to chamber 140 in the event that sample component 120 has not been inserted into housing 110 via entry tube 142 and/or connected to interface 144. The order in which control mechanism permits two or more reagents to flow to chamber 140 via channels 135 may be predetermined by the manufacturer of device 100 and/or may be set or programmed by a practitioner of device 100.

Additionally, or alternatively, control mechanism 150 may be connected to some or all of buttons 132 and/or chambers 130 to prevent two or more reagents from flowing to chamber 140 in an order that is different than a predetermined order. Also, or alternatively, two or more control mechanisms 150 may be distributed among two or more buttons 132 and/or chambers 130. In one example, each button 132 and/or chamber 130 may be connected to and/or integrated with a respective, different control mechanism 150. In this example, each control mechanism 150 may be mechanically, electrically, or optically interconnected to prevent the two or more reagents from flowing to chamber 140 in an order that is different than the predetermined order. Additionally, or alternatively, control mechanism 150 may include a processor and/or central processing unit that executes instructions and communicates with button 132 and/or chamber 130 to ensure that two or more reagents are delivered to chamber 140 in the predetermined order.

Figure 2B:
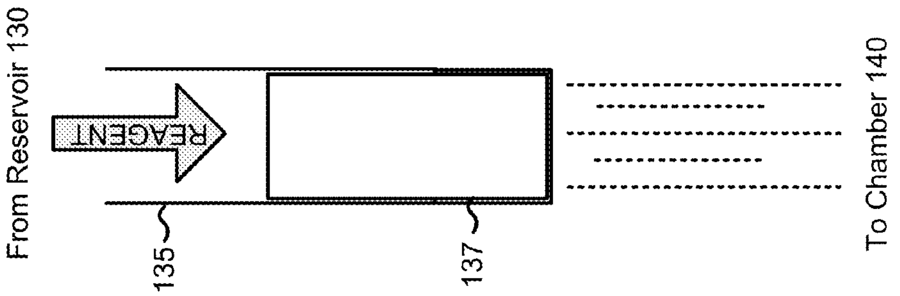
FIGS. 2A-2E are diagrams of example nozzles and channel components of an assay device through which reagents from a reservoir may flow.
Figure 2A:
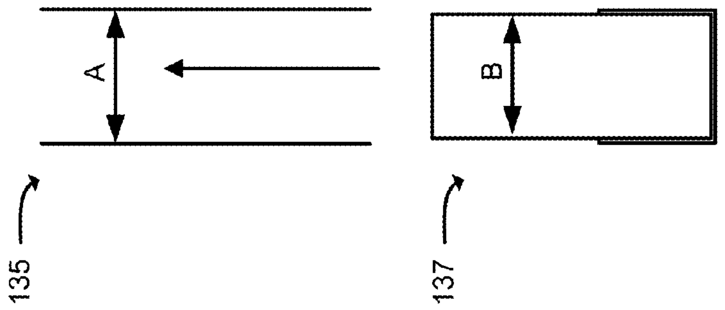

FIGS. 2A-2E are diagrams of example nozzles 137 and channels 135 through which reagents from reservoir 130 flow and enter chamber 140. As shown in FIG. 2A, nozzle 137 may be inserted into an end of channel 135 (e.g., as shown by the upward pointing arrow) that is opposite another end of channel 135 to which reservoir 130 is connected. Channel 135 may have a particular diameter or cross sectional area (e.g., shown as A) and nozzle 137 may have a diameter or cross sectional area (e.g., shown as B). Nozzle 137 may, in one example, include a cross sectional area that is uniform along the axis of nozzle 137. In another example implementation, nozzle 137 may include a cross sectional area that changes along the axis of nozzle 137.

As shown in FIG. 2B, nozzle 137 is inserted into channel 135 and reagent, from reservoir 130, is flowing from channel 135, through nozzle 137, and into chamber 140. The flow of reagent may include certain flow parameters such as a particular velocity, flow rate (e.g., mass flow), acceleration, pressure, etc. as the reagent flows into chamber 140. The flow parameters may, for example, include instantaneous flow parameters that are measured at a particular point in time; a combination of flow parameters that are measured over a period of time (e.g., an average, a mean, etc. flow parameters); a change in flow parameters (e.g., a difference in two or more instantaneous flow parameters, a rate of change in flow parameters, etc.); etc. In one example, the cross sectional area along the axis of nozzle 137 may be uniform, as shown in FIG. 2B, which may have minimal effect (e.g., less than a threshold) on the flow parameters relative to such parameters when the reagent is flowing through channel 135. Also, or alternatively, the uniform cross sectional area of nozzle 137 may cause the reagent to flow directly and/or without a spray pattern into chamber 140 as shown by the parallel dotted lines in FIG. 2B, which may represent the direction of the flow of the reagent as it enters chamber 140.

Figure 2C:
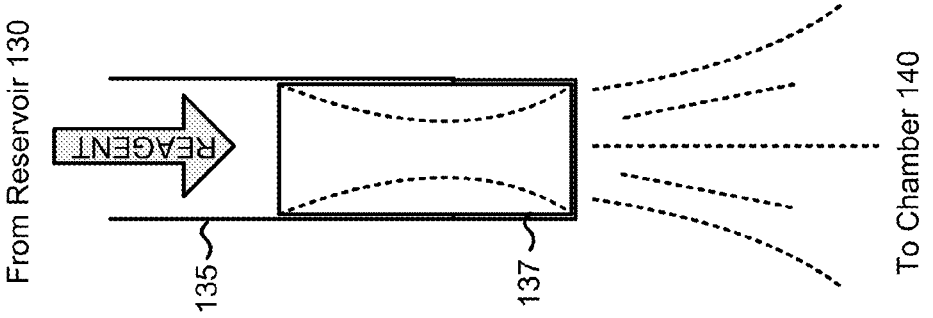
Figure 2D:
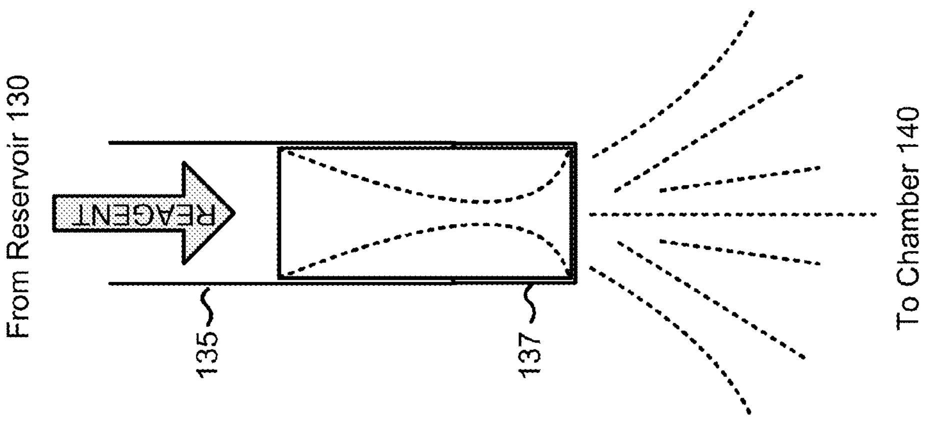
Figure 2E:
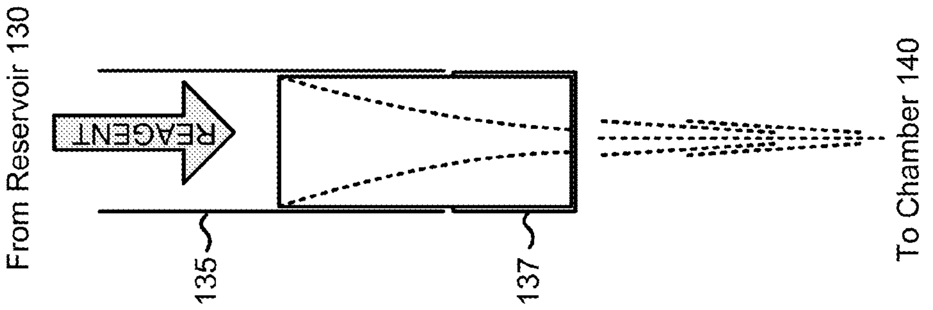

As shown in FIGS. 2C-2E, varying the cross sectional area along the axis of nozzle 137 may change the manner in which the reagent flows into chamber 140 by an amount that is greater than the threshold. For example, as shown in FIGS. 2C and 2D, when nozzle 137 includes a venturi shape in which the diameter and/or cross sectional area is the greatest as the reagent enters or exits nozzle 137, nozzle 137 may cause a change in velocity, flow rate, acceleration or pressure, relative to values of such flow parameters when the reagent is flowing through channel 135. Such a change in the flow parameters may correspond to an amount that is greater than the threshold. The change in flow parameters and/or spray pattern may permit the manufacturer or vendor of device 100 to tune the velocity, flow rate, acceleration or pressure of reagents for particular types of applications or assays, and/or for different temperatures and viscosities of reagents being used by a practitioner.

Additionally, or alternatively, the venturi shape may also, or alternatively, cause the reagent to flow into the chamber in a divergent or conical spray pattern as shown by the diverging and non-parallel dotted lines in FIGS. 2C and 2D. Such divergent spray patterns may permit the manufacturer or vendor of device 100 to tune the spay pattern as the reagent enters chamber 140 for the purposes of affecting the manner in which the reagent is directly applied and/or saturates the sample.

As shown in FIG. 2E, nozzle 137 may include other shapes which may have different effects on the flow parameters or spray pattern of the reagent. For example, a cross sectional area resembling a funnel, as shown in FIG. 2E, may change the flow parameters (e.g., increase velocity, restrict flow, decrease pressure, etc.) while causing reagent to enter chamber 140 in a converging stream or "jet" pattern as shown by the converging dotted lines of FIG. 2E, which may provide the vendor or manufacturer additional flexibility to tune device 100 for particular assays, reagents, viscosities, samples, thermal environments, etc.

The number of components and/or cross sectional areas and shapes illustrated in FIGS. 2A-2E, are provided for explanatory purposes only. In practice, there may be additional components and/or cross sectional areas and shapes, fewer components and/or cross sectional areas and shapes, different components and/or cross sectional areas and shapes, or differently arranged components and/or cross sectional areas and shapes than illustrated in FIGS. 2A-2E.

Also, in some implementations, one or more of the components and/or cross sectional areas and shapes may perform one or more functions described as being performed by another one or more of the components and/or cross sectional areas and shapes. For example, the cross sectional areas and shapes could be integrated directly into channel 135, which may negate the need to include nozzle 137 and/or integrate such cross sectional areas and/or shapes into nozzle 137.

Figure 3A:
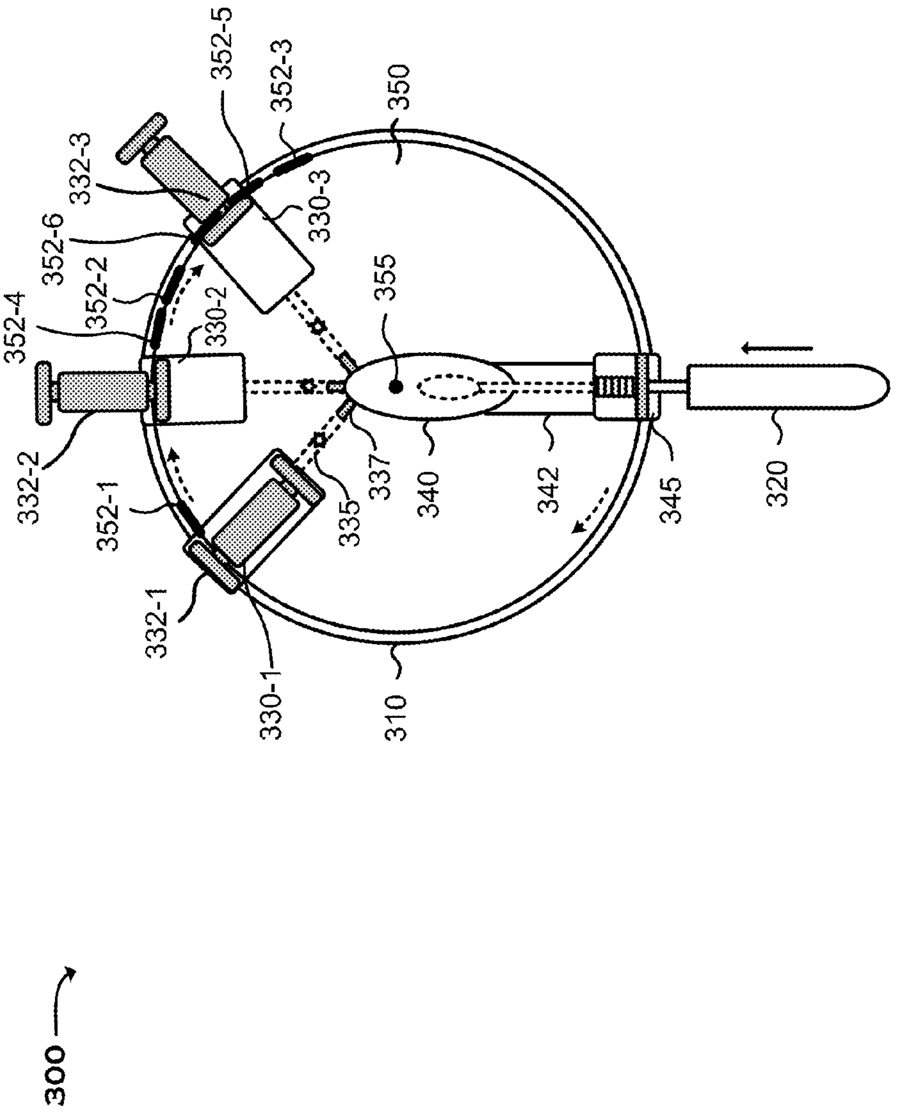
FIG. 3A is a diagram of an example assay device in which the systems and/or methods, described herein, may be implemented.

FIG. 3A is a diagram of an example assay device 300 (hereinafter "device 300") in which the systems and/or methods, described herein, may be implemented. As shown in FIG. 3A, device 300 may include all or a portion of the components described as being included in device 100 of FIG. 1. For example, device 300 may include a housing component 310 (hereinafter referred to as "housing 310"), a sample component 320, a group of reagent reservoir components 330 (collectively referred to herein as "reservoirs 330," and individually as "reservoir 330"), a group reagent button components 332 (collectively referred to herein as "buttons 332" and individually as "button 332"), a group of reagent channel components 335 (collectively referred to herein as "channels 335," and individually as "channel 335"), a group of flow control nozzle component 337 (hereinafter referred to collectively as "nozzles 337" and individually as "nozzle 337"), an assay test chamber 340 (hereinafter referred to as "chamber 340"), an interface 345, a reagent control mechanism 350 (hereinafter referred to as a "control mechanism 350"); and an axis 355.

The number of components, illustrated in FIG. 3A, is provided for explanatory purposes only. In practice, there may be additional components, fewer components, different components, or differently arranged components than illustrated in FIG. 3A. For example, locks 352-2 and 352-4 may be combined into a single lock 352, and/or locks 352-3, 352-5, and 352-6 may be combined into a single lock 352. Also, in some implementations, one or more of the components of device 300 may perform one or more functions described as being performed by another one or more of the components of device 300.

All or a portion of the functionality of the components of device 300 may generally correspond to some or all of the functionality of corresponding components included in device 100 of FIG. 1. For example, housing 310 may correspond to housing 110 of FIG. 1; sample component 320 may correspond to sample component 120 of FIG. 1; reservoir 330 may correspond to reservoir 130 of FIG. 1; button 332 may correspond to button 132 of FIG. 1, channel 335 may correspond to channel 135 of FIG. 1, nozzle 337 may correspond to nozzle 137 of FIG. 1, chamber 340 may correspond to chamber 140 of FIG. 1; interface 345 may correspond to interface 144 in FIG. 1, and control mechanism 350 may correspond to control mechanism 150 in FIG. 1.

By way of example, a practitioner of device 300 may, in a manner similar to that described above with respect to FIG. 1, use sample component 320 collect a sample from a subject, object, animal, etc. and may insert sample component into housing 310 (e.g., via entry tube 342 into chamber 340) to cause sample 120 to connect to interface 345.

Housing 310 may correspond to a shallow cylinder with a first end that is closed and a second, opposite end that is open. The depth of the cylinder may, in one example, be less than half the radius of the cylinder. Housing 310 may include one or more reservoirs 330 that store one or more reagents. Each reservoir 330 may be associated with a respective button 332 (or a compressible surface) that when depressed, causes reagent to flow from reservoir 330, via channel 335 and nozzle 337, into chamber 340. The open end of the cylinder may have a radius or diameter that enables control mechanism 350 to fit inside of housing 310 and be rotatably attached thereto about axis 355.

Control mechanism 350 may be made of a rigid material (e.g., plastic, metal, composite, ceramic, etc.) and may include a shallow cylinder with a first end that is closed and a second, opposite end that is open. The shallow cylinder may, in one example, have a depth that is less than half of the radius of the cylinder. Control mechanism 350 may be rotatably connected to housing 310 about which housing 310 and control mechanism can rotate relative to each other about axis 355. The open end of control mechanism may fit within the open end of housing 310. In one example, the open end of housing 310 may include a flange, bevel, or some other structure that precludes control mechanism 350 from coming apart or separating from housing 310 while permitting control mechanism 350 to rotate within housing 310.

Control mechanism 350 may include one or more locks 352 located within or attached to a cylinder wall of control mechanism 350. When any portion of lock 352 coincides, makes contact, and/or is aligned with a location of button 332 and/or reservoir 330 (e.g., when a practitioner rotates housing 310 and/or control mechanism 350 about axel 355), button 332 and/or reservoir 330 cannot be compressed and are in a locked mode. In one example, button 332 may be a trumpet valve (e.g., a syringe-like device) that includes a plunger associated with a first diameter that, when pressed by a practitioner, cause reagent to flow from reservoir 330 to test chamber 340. Lock 332 may include an aperture with a second diameter that is less than the first diameter to preclude button 332 from being compressed when lock 332 is at a position that coincides, makes contact, and/or is aligned with button 332 or reservoir 330. The locked mode may provide a fail-safe mechanism that prevents reagent from flowing from reservoir 330 to chamber 340. If no lock coincides, makes contact, or is aligned with the location of reservoir 330 and/or button 332, button 332 can be compressed and reagent may flow from reservoir 330 to chamber 340.

In one example, a respective lock 352 may be positioned at a location associated or aligned with each button 332, which may represent a locked mode or default configuration of device 300 that disables all buttons 332 or reservoirs 330 from being compressed. Additionally, or alternatively, when sample component 320 is inserted into housing 310 and/or becomes connected to interface 345, interface 345 may cause control mechanism 350 to rotate about axis 355. This rotation (e.g., a first rotation) may cause a first lock 352 (e.g., lock 352-1), corresponding to a first button 332-1 and/or first reservoir 330-1, to rotate to a location that does not correspond to or align with button 332-1 or reservoir 330-1. Thus, the first rotation may enable button 332-1 and/or reservoir 330-1 to be depressed by a practitioner of device 300, which may cause a first reagent, stored in the reservoir 330-1, to flow to chamber 340. Device 300 may also, or alternatively include a first indicator 133 (not shown in FIG. 3A) that changes in appearance when the first reagent flows to chamber 340, when button 332-1 is pressed, and/or when reservoir 330-1 is compressed.

Additionally, or alternatively, second and third locks 352 (e.g., locks 352-2 and 352-3, respectively), each corresponding to or aligning with locations associated with second and third buttons 332 (e.g., buttons 332-2 and 332-3), respectively and/or second and third reservoirs 330 (e.g., reservoirs 330-2 and 330-3) respectively, may likewise rotate to positions that do not correspond to or are mis-aligned with locations associated with buttons 332-2 and 332-3 and/or reservoirs 330-2 and 330-3. To ensure that second and third buttons 332 cannot be pressed and/or second and third reservoirs 330 cannot be compressed, fourth and fifth locks 352 (e.g., locks 352-4 and 352-5, respectively) may be positioned on control mechanism 350 to permit locks 352-4 and 352-5 to rotate to locations associated or aligned with buttons 332-2 and 332-3 respectively and reservoirs 330-2 and 330-3, respectively.

Additionally, or alternatively, when the practitioner of device 300 presses button 332-1 and/or causes reservoir 330-1 to compress, button 332-1 and/or reservoir 330-1 may cause control mechanism 350 to rotate (e.g., a second rotation) which may cause lock 352-4 to move to a location that does not correspond to and/or is mis-aligned with button 332-2 or reservoir 330-2. The second rotation may, therefore, cause button 332-2 and/or reservoir 330-2 to become unlocked thereby enabling the practitioner to press button 332-2 and/or compress reservoir 330-2 causing a second reagent to flow to chamber 340. Device 300 may also, or alternatively include a second indicator 133 (not shown in FIG. 3A) that changes in appearance when the second reagent flows to chamber 340, when button 332-2 is pressed and/or when reservoir 330-2 is compressed. The second rotation may also, or alternatively, cause a sixth lock 352-6 to move to a position that corresponds to or is aligned with the location of button 332-3 and/or reservoir 330-3 thereby preventing the practitioner from pressing button 332-3 and/or compressing reservoir 330-3.

Additionally, or alternatively, when the practitioner of device 300 presses button 332-2 and/or causes reservoir 330-2 to compress, button 332-2 and/or reservoir 330-2 may cause control mechanism 350 to rotate (e.g., a third rotation) which may cause lock 352-6 to move to a location that does not correspond to or align with button 332-3 and/or reservoir 330-3. The third rotation may, therefore, cause button 332-3 and/or reservoir 330-3 to become unlocked thereby enabling the practitioner to press button 332-3 and/or compress reservoir 330-3 and causing a third reagent to flow to chamber 340. Device 300 may also, or alternatively, include a third indicator 133 (not shown in FIG. 3A) that changes in appearance when the third reagent flows to chamber 340, when button 332-3 is pressed, and/or when reservoir 330-3 is compressed Control mechanism 350 and control locks 352 may, therefore, be configured by the manufacturer or vendor to enable the two or more reagents to flow to chamber 340 in a particular, predetermined or programmable order and may also, or alternatively, prevent any of the reagents from flowing to chamber 340 in an order that is different than the predetermined or programmable order.

While FIG. 3A illustrates adjacent locks 352 (e.g., locks 352-2 and 352-4, and locks 352-6, 352-5, and 352-3) as being separate, discrete locks 352, in another implementation, adjacent locks may be combined into a single lock 352 with a length approximately equal to the sum of the lengths of the adjacent locks.

Figure 3B:
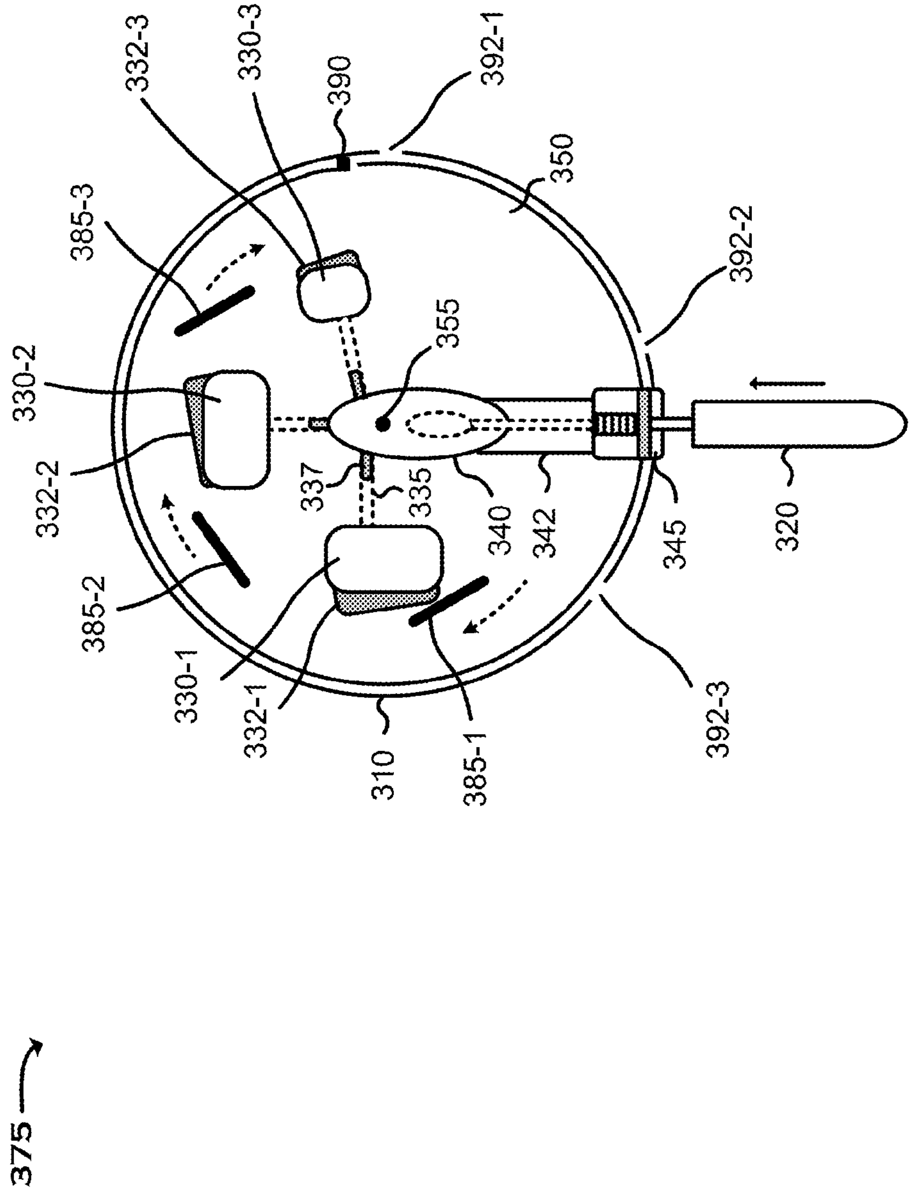
FIG. 3B is a diagram of another example assay device in which the systems and/or methods, described herein, may be implemented.

FIG. 3B is a diagram of another example assay device 375 (hereinafter "device 375") in which the systems and/or methods, described herein, may be implemented. As shown in FIG. 3B, device 375 may include a collection of components described above with respect to FIG. 3A including housing 310, sample 320, reservoirs 330-1, . . . 330-3, buttons 332-1, . . . , 332-3, a group of channels 335, a group of nozzles 337, chamber 340, interface 345, reagent control mechanism 350 (hereinafter referred to as a "control mechanism 350"); and axel component 355. Additionally, or alternatively, device 375 may include a group of members 385-1, . . . , 385-3 (hereinafter referred to individually as "member 385" and collectively as "members 385"), and a lock mechanism 390.

Member 385 may include a structural member of sufficient rigidity to be attached to control mechanism 350 and cause reservoir 330 and/or button 332 to be compressed to enable a reagent to flow to chamber 340. Member 385 may be attached to control mechanism 350 at approximately a right angle to a closed end of the cylinder on which control mechanism is based. A single member 385 may be attached to compress each reservoir 330 in succession as control mechanism 350 rotates within housing 310. For example, member 385 may rotate as control mechanism 350 rotates within housing 310. Member 385 may come into contact with and may cause reservoir 330 and/or button 332 to be compressed as control mechanism 350 rotates. In this example, a predetermined order in which the reservoirs are installed within housing 310 may correspond to the order in which single member 385 compresses reservoirs 330-1, 330-2, and 330-3.

Additionally, or alternatively, a respective member 385 may be attached to control mechanism 350 for each reservoir 330. For example, member 385-1 may be attached to compress reservoir 330-1, member 385-2 may be attached to compress reservoir 330-2, member 385-3 may be attached to compress reservoir 330-3, etc. The location at which each member 385 is attached to control mechanism 350 may determine an order in which reservoirs 330 are compressed and/or reagents are caused to flow to chamber 340.

Lock mechanism 390 may include any device that can preclude control mechanism 350 from rotating relative to housing 310. In one example, lock mechanism 390 may include a spring and a pin attached thereto. The spring may, for example, correspond to a portion of material (e.g., a tab, flap, stub, etc.) of the cylinder wall of control mechanism that provides a force that presses the pin against an interior surface of the wall of housing 310. When control mechanism 350 is rotated to cause a first reservoir 330-1 and/or first button 332-2 to be compressed (e.g., by member 385), the spring may cause the pin to protrude through an first aperture 392-1 in the wall of housing 310 causing the control mechanism 350 to stop rotating while a first reagent is flowing to test chamber 340. A practitioner, associated with device 375, may press on the pin to enable control mechanism 350 to be rotated to a second rotational position that causes a second reservoir 330-2 and/or second button 332-2 to be compressed. Lock mechanism 390 may engage, such that the spring may cause the pin to protrude through a second aperture 392-2 within housing 310 to prevent control mechanism 350 from rotating while a second reagent is flowing to the test chamber.

The number of components, illustrated in FIG. 3B, is provided for explanatory purposes only. In practice, there may be additional components, fewer components, different components, or differently arranged components than illustrated in FIG. 3B. For example, members 385-1, . . . , 385-3 may be combined into a single lock member 385. Also, in some implementations, one or more of the components of device 375 may perform one or more functions described as being performed by another one or more of the components of device 375.

The foregoing description provides illustration and description, but is not intended to be exhaustive or to limit the implementations to the precise form disclosed. Modifications and variations are possible in light of the above disclosure or may be acquired from practice of the embodiments.

It will be apparent that technologies and/or techniques, as described above, may be implemented in many different forms of hardware in the implementations illustrated in the figures. The actual or specialized hardware used to implement these technologies and/or techniques is not limiting of the embodiments—it being understood that hardware can be designed to implement the technologies and/or techniques based on the description herein.

It should be emphasized that the terms "comprises"/"comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the article "a" and "an" are intended to include one or more items and may be used interchangeably with "one" or "more." Where only one item is intended, the term "one" or similar language is used. Further, the phrase "based on" is intended to mean "based, at least in part, on" unless explicitly stated otherwise.

What is claimed is:

1. An assay device to perform an assay on a sample, the assay device comprising:
- a first cylinder that includes a first end that is closed and a second, opposite end that is open, the first cylinder includes one or more reservoirs and a test chamber,
  - the one or more reservoirs being compressible and storing one or more reagents, and
  - the test chamber being connected to the one or more reservoirs, and receiving the sample on which the assay is to be performed; and
- a second cylinder includes a third end that is closed and a fourth, opposite end that is open, the fourth end fitting within the second end and enabling the second cylinder to be attached to, and to rotate within, the first cylinder,
  - the third end including at least one member that compresses the one or more reservoirs, in a predetermined order, as the second cylinder is rotated within the first cylinder, compressing the one or more reservoirs causing the one or more reagents to flow to the test chamber according to the predetermined order.

2. The assay device of claim 1, where the second cylinder further includes:
- a locking mechanism to prevent the second cylinder from rotating relative to the first cylinder, the locking mechanism including:
  - a spring and a pin to which the spring is attached, the spring causing the pin to protrude through a first aperture, associated with the first cylinder, when the second cylinder is rotated to a first position relative to the first cylinder,
  - the first position permitting the at least one member to compress a first reservoir, of the one or more reservoirs.

3. The assay device of claim 2, where the pin protrudes, through the first aperture in a manner that enables a practitioner, associated with the device, to press the pin to permit the second cylinder to be rotated to a second position, relative to the first cylinder, at which the spring causes the pin to protrude through second aperture associated with the first cylinder,
- the second position permitting the at least one member to compress a second reservoir of the one or more reservoirs.

4. The assay device of claim 1, where the at least one member is attached at approximately a right angle to the third end.

5. The assay device of claim 1, where the location at which the at least one member is attached to the third end enables the at least one member to make contact with or compress a flexible material or a button, associated with each of the reservoirs, to cause the one or more reagents to flow to the test chamber.

6. The assay device of claim 1, where an order in which the at least one member makes contact with or compresses the one or more reservoirs, when the second cylinder is rotated within the first cylinder, corresponds to the predetermined order.

7. The assay device of claim 1, where the at least one member includes at least one of:
- a first member to compress a first reservoir of the one or more reservoirs, or
- a second member to compress a second reservoir of the one or more reservoirs.

8. The assay device of claim 7, where the predetermined order in which the one or more reservoirs are compressed is based on a first location at which the first member is attached to the third side relative to the first reservoir and a second location at which the second member is attached to the third side relative to the second reservoir.

9. The assay device of claim 1, where the predetermined order in which the one or more reservoirs are compressed is based on an order in which the one or more reservoirs are installed in the first cylinder.

10. The assay device of claim 1, where the assay device further comprises at least one of:
- one or more nozzles through which the one or more reagents flows into the test chamber or on the sample based on one or more flow rates or spray patterns associated with the one or more nozzles.

* * * * *